United States Patent
Cui et al.

(10) Patent No.: US 8,558,061 B2
(45) Date of Patent: Oct. 15, 2013

(54) INDUCED CHROMOSOME DOUBLING IN PLANTS

(75) Inventors: Yunxing Cory Cui, Carmel, IN (US); Paul R. Schmitzer, Indianapolis, IN (US); David H. Young, Carmel, IN (US)

(73) Assignee: Agrigenetics, Inc., Indianapolis, IN (US)

( * ) Notice: Subject to any disclaimer, the term of this patent is extended or adjusted under 35 U.S.C. 154(b) by 599 days.

(21) Appl. No.: 12/646,064

(22) Filed: Dec. 23, 2009

(65) Prior Publication Data
US 2010/0169999 A1    Jul. 1, 2010

Related U.S. Application Data

(60) Provisional application No. 61/141,094, filed on Dec. 29, 2008, provisional application No. 61/289,159, filed on Dec. 22, 2009.

(51) Int. Cl.
*A01H 1/08* (2006.01)
*A01N 47/10* (2006.01)
*A01N 33/02* (2006.01)
*A01N 33/18* (2006.01)
*A01N 33/24* (2006.01)

(52) U.S. Cl.
USPC ........ 800/299; 800/275; 800/276; 800/320.1; 435/424; 435/430.1; 504/143; 514/638; 514/716; 514/717

(58) Field of Classification Search
None
See application file for complete search history.

(56) References Cited

U.S. PATENT DOCUMENTS 3,978,222 A * 8/1976 Enders et al. .................. 514/331
5,866,513 A    2/1999 Michelotti et al.
7,135,615 B2 * 11/2006 Kato ............................. 800/276

OTHER PUBLICATIONS

Halfmann et al. The Journal of Cotton Science 11: 60-67 (2007).*
Young et al. Bioorganic and Medicinal Chemistry Letters 11: 1393-1396 (2001).*
Mahill et al. Crop Science 24(2): 271-277 (1984).*
Halfmann et al. 2007a. chemical structure of compound RH 9472 disclosed in Journal of Cotton Science 11(1): 60-67.*
Dhooghe, E., et al., "Mitotic chromosome doubling of plant tissues in vitro," Plant Cell Tiss Organ Cult, 2011, pp. 359-373, vol. 104.

* cited by examiner

*Primary Examiner* — David T Fox
(74) *Attorney, Agent, or Firm* — Eric J. Kraus; TraskBritt P.C.

(57) ABSTRACT

Methods to generate doubled haploid plants and plant components using low mammalian toxicity chromosome doubling agents are disclosed. Chromosome doubling agents provide low mortality rates and higher chromosome doubling rate in plants.

17 Claims, No Drawings

INDUCED CHROMOSOME DOUBLING IN PLANTS

CROSS-REFERENCE TO RELATED APPLICATIONS

This Application is a Non-Prov of Prov (35 USC 119(e)) application 61/141,094 filed on Dec. 29, 2008 and 61/289,159 filed on Dec. 22, 2009.

FIELD

The present invention generally relates to plant breeding and generating doubled haploid plants.

BACKGROUND

Traditional plant breeding to include parental lines for desirable traits involves crossing selected parental lines to introduce those desirable traits into the progeny of the cross. In a crossing-based approach, often, not only the desirable trait is transferred to the progeny but some randomization of the genomes of both parental lines occurs. This results in a wide segregation and variation of morphology and other traits of the progeny, which are not predictable. The uncontrolled variation renders the progeny selection process very long, cumbersome and laborious especially if the desired traits are not expressed early in the progeny or if the desired trait is recessive.

In an effort to minimize the random variation, breeders prefer homozygous parental lines (inbreds) so that the genetic make up of the $F_1$ generation is more predictable. The inbreds with a desirable trait are generated by back-crossing a heterozygote with its parental lines, followed by segregation selection and repeated back-crossing. However, this repeated back-crossing is also very long, usually up to 6 to 7 times, depending on the plant, would produce a homozygous plant with the desired trait. Of course, the time scale involved here is dictated by the rate at which plants grow to maturity and set seed and several years can be necessary to produce the desired homozygous parent line.

Haploid plants contain one half of the usual complement of genes. Normal plants are diploid in that they have two complete sets of chromosomes, one from each parent. Polyploid plants have more than two sets of chromosomes. Haploid plants are capable of growing to maturity but are generally sterile. There are several known methods of generating haploid plants.

One way to obtain homozygous plants without the need to cross two parental lines followed by a long selection of the segregating progeny, and/or multiple back-crossings is to produce haploids and then double the chromosomes to form doubled haploids. The production of doubled haploid plants yields highly uniform inbred lines and is especially desirable as an alternative to sexual inbreeding of longer-generation crops. By producing doubled haploid progeny, the number of possible gene combinations for inherited traits is more manageable. Thus, an efficient doubled haploid technology can significantly reduce the time and the cost of inbred and cultivar development. Chemicals such as colchicines are used as chromosome doubling agents. However, due to their mammalian toxicity and low efficiency, their use in plant breeding has been limited. Therefore, agents to induce chromosome doubling in plants with low mammalian toxicity are desirable.

SUMMARY

Methods for generating doubled haploid plants, seeds, cells, and cell cultures are provided. The methods disclosed herein increase the efficiency of the doubled haploid generation by increasing the number of doubled haploids obtained, exhibit low mammalian toxicity and reduced the time required to produce the doubled haploids.

DETAILED DESCRIPTION OF THE INVENTION

Methods to obtain doubled haploid plants or plant components using low mammalian toxicity chromosome doubling agents are disclosed. Contacting a haploid plant component e.g., whole plant or a collection or population of plant cells with low mammalian toxicity chromosome doubling agents results in the generation of doubled haploid plants or plant components.

Chemicals listed in the U.S. Pat. No. 5,866,513 to Michelotti et al., are used to generate doubled haploid plants. The disclosure of U.S. Pat. No. 5,866,513 is incorporated herein by reference in its entirety. For example, Table I and Ia on Cols. 3 and 4, 5 and 6, and 7 and 8 of U.S. Pat. No. 5,866,513 list about 76 specific example compounds and each of those compounds is herein incorporated by reference in its entirety. In addition, methods of making some of the specific examples as described in Cols. 11-22 are incorporated herein by reference in its entirety.

In one embodiment a method is described for generating doubled haploid plant cells comprising contacting a population of haploid plant cells with a composition comprising a low mammalian toxicity chromosome doubling agent of following formula:

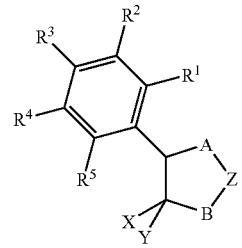

wherein $R^1$, $R^2$, $R^3$, $R^4$, and $R^5$ are in each instance independently selected from the group consisting of hydrogen, alkoxy, nitro, halo, alkyl, and haloalkyl; A and B are each independently $CH_2$, $CHR^a$ or $CR^aR^b$, wherein $R^a$ and $R^b$ are in each instance independently selected from the group consisting of hydrogen, halogen, cyano, alkyl, alkenyl, alkoxy, haloalkyl, haloalkoxyl, alkylcarbonyl and alkoxycarbonyl, or $R^a$ and $R^b$ together with the attached carbon form a cycloalkylene; Z is CH=CH, $CH_2$—$CH_2$, $CH_2$=CH($CH_3$), or $CR^d$=$CR^e$, where $R^d$ and $R^e$ are each independently hydrogen, alkyl or $R^d$ and $R^e$ together with the attached carbons form a cycloalkylene; X and Y are each independently selected from the group consisting of hydrogen, $NO_2$, CN, halogen, alkylcarbonyl, alkoxycarbonyl, and $CH_2$—$NO_2$, provided that X and Y are not both hydrogen; and diastereomers and stereoisomers thereof.

In a preferred embodiment a method is described for generating doubled haploid plant cells comprising contacting a population of haploid plant cells with a composition comprising a low mammalian toxicity chromosome doubling agent of following formula:

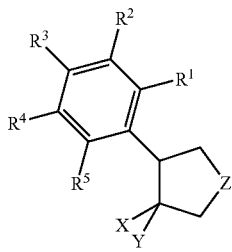

wherein $R^1$, $R^2$, $R^3$, $R^4$, and $R^5$ are in each instance independently selected from the group consisting of hydrogen, alkoxy, nitro, halo, alkyl, and haloalkyl; Z is CH=CH, $CH_2$—$CH_2$, $CH_2$=CH($CH_3$), or $CR^d$=$CR^e$, where $R^d$ and $R^e$ are each independently hydrogen, alkyl or $R^d$ and $R^e$ together with the attached carbons form a cycloalkylene; X and Y are each independently selected from the group consisting of hydrogen, $NO_2$, CN, halogen, alkylcarbonyl, alkoxycarbonyl, and $CH_2$—$NO_2$, provided that X and Y are not both hydrogen; and diastereomers and stereoisomers thereof.

In one embodiment the low mammalian toxicity chromosome doubling agent comprises a compound of the following formula and diastereomers and stereoisomers thereof:

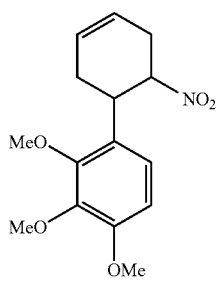 [SMILES: COc1ccc(C2CC=CCC2[N+](=O)[O-])c(OC)c1OC]

Suitable dosage for the low mammalian toxicity chromosome doubling agents for the seedling soak method disclosed herein include for example 0.01 μM, 0.5 μM, 1 μM, 2 μM, 3 μM, 4 μM, 5 μM, 10 μM, 15 μM, 20 μM, 25 μM, 30 μM, 35 μM, 40 μM, 45 μM, 50 μM, 60 μM, 70 μM, 80 μM, 90 μM, 100 μM, 125 μM, 150 μM, 200 μM, 500 μM, and 1000 μM. Suitable ranges also include for example, 0.1-10 μM, 1-100 μM, 5-125 μM, 25-200 μM, 50-500 μM, 15-150 μM and 1-10,000 μM.

The low seedling mortality of the chromosome doubling agents disclosed herein, when compared to colchicine (e.g., at 0.06% w/v) can range for example from less than 10% to about 40% or less than about 5% to about 20% or less than about 15% to about 25% or less than 50% of the total number of seedlings or plant cells treated.

Suitable dosage for the low mammalian toxicity chromosome doubling agents for the seedling foliar application method disclosed herein include for example 3.5 g ai/ha, 70 g ai/ha, 140 g ai/ha, 280 g ai/ha. Suitable application rates ranges include for example 5 g ai/ha to 1120 g ai/ha, and more preferably to 2,800 g ai/ha.

The low mammalian toxicity of the chromosome doubling agents disclosed herein may show $LD_{50}$ (rat) that is greater than or equal to 400 mg/kg or 500 mg/kg or 600 mg/kg or 700 mg/kg or 800 mg/kg or 900 mg/kg or 1000 mg/kg. Suitable $LD_{50}$ (rat) range may also include 200-1000 mg/kg or 100-1000 mg/kg or greater than 100 mg/kg or greater than 1000 mg/kg.

A haploid plant has a single set of chromosomes and the reduced number of chromosomes (n) in the haploid plant is equal to that in the gamete. For example, a haploid corn plant has 10 chromosomes, instead of 10 pairs of chromosomes as in a normal diploid corn plant. A diploid plant has two sets of chromosomes and the chromosome number (2n) is equal to that in the zygote. Each chromosome in a pair is derived from the maternal or paternal line.

A doubled haploid ("DH") or a doubled haploid plant or cell refers to the plant or its component developed by the doubling of a haploid set of chromosomes. A doubled haploid plant is considered a homozygous plant. A plant is considered to be doubled haploid even if the entire vegetative part of the plant does not consist of the cells with the doubled set of chromosomes, as long as the double haploid plant is fertile. The haploid plant may be derived from any plant and may be derived from a heterozygous plant. Such a heterozygous plant may or may not be a member of a heterogeneous population of plants, such as from an open pollinated population of plants. The heterozygous plant may be obtained from any heterozygous materials including local varieties, composites of different genetic backgrounds and other collections of plants.

A "haploid immature embryo" is defined as the embryo formed after one sperm nucleus from a pollen grain fuses with the polar nuclei in the embryo sac to create a triploid (3N) endosperm and before dry down.

A "doubled haploid embryo" is an embryo that has one or more cells that contain 2 sets of homozygous chromosomes. "Callus" refers to an undifferentiated proliferating mass of cells or tissue.

The phrase "contacting" includes reference to "direct contact" and "indirect contact." For example, the medium comprising a doubling agent may have direct contact with the haploid cell or the medium comprising the doubling agent may be separated from the haploid cell by a barrier such as a filter paper, plant tissue, or other cells thus the doubling agent is transferred through the filter paper or cells or tissue to the haploid cell. Contacting is achieved in any suitable manner, e.g., hydroponic treatment of roots, spraying, injecting, infiltrating, soaking, and wetting.

The term "plant" includes reference to whole plants and plant components (e.g., leaves, stems, roots, pollen, etc.), seeds and plant cells and progeny of same. "Plant cell," as used herein includes, without limitation, seeds, suspension cultures, embryos, meristematic regions, callus tissue, leaves, roots, shoots, gametophytes, sporophytes, pollen, and microspores. Plants that are capable of being used in the methods disclosed herein include both monocotyledonous and dicotyledonous plants.

Suitable plants include for example, monocotyledonous plants, such as a maize, rice, wheat, barley, oats, onion, rye, millet, sorghum, sugarcane, lily or turfgrass plant.

The methods disclosed herein generally produce a high frequency of doubled haploid plants that are fertile.

In an embodiment, methods to obtain a doubled haploid embryo, seed, or plant by contacting a haploid embryo with a doubling agent and obtaining a doubled haploid embryo, seed, or plant are disclosed.

In another embodiment, methods to obtain a doubled haploid cell culture from a suitable plant component e.g., doubled haploid tissue culture are disclosed.

A method to obtain a haploid plant component for inducing chromosome doubling includes for example, a) pollinating ovules, or stigmas, of a plant with pollen from an inducer line, wherein the inducer line has a marker gene that is expressed in embryos and/or endosperm tissue; and b) selecting a haploid embryo that has no marker gene expression. Pollination of the plant can be by any method, including natural cross-pollination and manual pollination.

Somatic haploid cells, haploid embryos, haploid seeds, or haploid seedlings produced from haploid seeds can be treated with a low mammalian toxicity chromosome doubling agent. Homozygous plants can be regenerated from haploid cells by contacting the haploid cells, such as embryo cells or callus produced from such cells, with chromosome doubling agents disclosed herein, to create homozygous doubled haploid cells. Treatment of a haploid seed or the resulting seedling or tissue generally may produce a chimeric plant or tissue, partially haploid and partially doubled haploid. It may be beneficial to nick the seedling before treatment with the doubling agent. When reproductive tissue contains doubled haploid cells, then doubled haploid seed is produced.

Haploid embryos, haploid seeds, somatic haploid cells or tissue from haploid plants can be harvested and transformed by any known means prior to treatment with a doubling agent. Transgenic homozygous plants, regenerated from the transformed cells can be treated with a chromosome doubling agent and growing the resulting seed/tissue to produce a doubled haploid plant having homozygous seeds.

In an aspect the inducer line may contain a scorable marker gene, for example colored markers in the endosperm, embryo, stem or leaves. Such markers include GUS, luciferase, CRC, anthocyanin genes such as A, C, R-nj, and others known in the art. When an inducer line with a scorable marker is crossed with the selected/desired line, the resulting haploid seeds will have for example, a colored endosperm with colorless embryo. It may be desirable to express the marker gene in the embryo. In particular, it may be desirable to express the marker gene in the early stage of development, about 8-15 days after pollination using an appropriate promoter such as an oleosin or a Lec1 promoter. Marker negative embryos are then selected to obtain haploid embryos. This method provides the advantage of obtaining haploid embryos without marker genes. Similarly, haploid inducer lines, such as RWS, KEMS, RWS, ZMS or KMS, can be transformed with a lethal gene that is expressed specifically in embryos of the mature seeds. After crossing the inducer line and the female parent the embryos of all the diploid seeds contain the inducible lethal gene, but the embryos of the haploid seeds do not contain the lethal gene. The diploid F1 seeds cannot germinate due to expression of the inducible lethal gene in their embryos. However, the haploid seeds can germinate normally because they do not contain the lethal gene in their embryos. The germinating seedlings are haploid.

One or more genes of interest that are reflective of the commercial markets and interests of those involved in the development of crops can be transformed or otherwise introduced in to a line of interest prior to generating a haploid seed or tissue by crossing with an inducer line. Such gene or genes of interest can also be transformed in to a haploid cell or tissue prior to treatment with a chromosome doubling agent to generate double haploid plant component.

General categories of genes of interest include for example include genes encoding agronomic traits, insect resistance, disease resistance, herbicide resistance, sterility, grain characteristics, and those involved in oil, starch, carbohydrate, or nutrient metabolism as well as those affecting for example kernel size, sucrose loading, and the like.

Another method is obtaining a doubled haploid seed that includes: a) obtaining a haploid seed by pollinating an ovule with an inducer line wherein the ovule comprises a set of maternal chromosomes and wherein the inducer line comprises a set of paternal chromosomes; b) contacting the haploid seed with a medium comprising a low mammalian toxicity chromosome doubling agent; c) selecting a doubled haploid seed wherein the doubled haploid seed comprises a triploid endosperm and a doubled haploid embryo. The doubled haploid seed produced by such a method wherein the triploid endosperm includes two sets of maternal chromosomes and one set of paternal chromosomes, and wherein the doubled haploid embryo has a first and second set of maternal chromosomes and wherein the first set of maternal chromosomes is homozygous to the second set of maternal chromosomes can be produced.

In an embodiment, a method of obtaining a population of doubled haploid maize plants include the following steps: a) obtaining a set of haploid kernels by pollinating an ear with an inducer line wherein the ear includes a set of maternal chromosomes and wherein the inducer line has a set of paternal chromosomes; b) contacting the set of haploid kernels with a medium having a low mammalian toxicity chromosome doubling agent; c) selecting a set of doubled haploid kernels wherein each kernel of the set of doubled haploid kernels includes a triploid endosperm and a doubled haploid embryo; d) growing the doubled haploid kernels into a population of doubled haploid maize plants. In other aspects, the ear can be removed before, during, or after pollination and placed into a solution. The doubling agent can come in contact with the ear after pollination and before or after the ear is removed from the plant. The chromosomal doubling agent may come into contact with the ear directly or indirectly, for example via filter paper or cotton or other suitable material.

A method of inbred selection may include the following steps: a) cross pollinating two inbred maize plants; b) growing the F1 seed; c) pollinating the F1 plant with an inducer line to produce haploid embryos; d) contacting the haploid embryos with a low mammalian toxicity chromosome doubling agent to produce doubled haploid embryos; e) generating doubled haploid plants; f) analyzing the doubled haploid plants for agronomic performance. The development of haploids step may also be done at later generations, e.g., F2, F3, F4, etc. Producing haploids from later generations allows for additional opportunities for recombination, if needed.

If a haploid embryo is used as a source material for treatment with a low mammalian toxicity chromosome doubling agent, embryo rescue is performed. Embryo rescue is performed by contacting an embryo with a medium containing nutrients and generating a plant. Phytohormones may or may not be included in the embryo rescue medium. A method of obtaining a transgenic doubled haploid embryo may comprise isolating a haploid embryo, transforming the haploid embryo, placing the haploid embryo on a medium comprising a chromosome doubling agent and selecting a transgenic doubled haploid embryo.

In any of these methods disclosed herein, the chromosomes can be doubled at the immature embryo stage, at the mature seed stage, or anytime between pollination of the plant and before the germination of the haploid seed.

In any of these methods the haploid embryo that undergoes chromosomal doubling may be isolated, may be in the seed or kernel, may be in the kernel on a slice of cob, may be on the ear or spike, or the haploid embryo may be in the kernel which is on the ear and on the plant. The doubling agent may reach the haploid embryo while the ear is on the plant and the plant is intact. For example, the doubling agent may be contacted directly or indirectly with the haploid embryo. In some cases the doubling agent can be transported by the plant. The plant may be grown hydroponically and the doubling agent can be taken up through the roots of the plant and transported to the haploid embryo. The seedlings may be initiated on soil or a growing medium and then transferred to a hydroponic solution where the doubling agent can be added. In another aspect of the method, the plant may be grown in soil or a growing medium and then the doubling agent is added to the soil or growing medium so that it can be transported to the haploid embryo.

The methods disclosed herein avoid time consuming selfing and crossing methods to obtain a homozygous trait of interest or a substantially homozygous plant. The methods can be used to produce doubled haploid populations that do not contain the residual heterozygosity of inbreds obtained though the traditional method of self pollination. The methods can be useful for functional genomics, such as knock-out analysis, functional analysis of recessive genes, gene replacement, homologous recombination, gene targeting, transgene stacking, and evaluating lethal versus non-lethal analysis of genes. In addition, the chromosome doubling agents disclosed herein are less toxic to mammalian systems compared to the traditional agent such as, colchicine.

Haploid plant production systems have been developed and practiced for various plants to generate haploid tissues including embryo, plants and seeds. The haploid plants or plant components from any genotype are generated by crossing a selected/desirable line (as female) with an inducer line (male). Exemplary inducer lines for maize include for example, Stock 6 (Coe, 1959, Am. Nat. 93:381 382; Sharkar and Coe, 1966, Genetics 54:453 464) RWS, KEMS (Deimling, Roeber, and Geiger, 1997, Vortr. Pflanzenzuchtg 38:203 224), or KMS and ZMS (Chalyk, Bylich & Chebotar, 1994, MNL 68:47; Chalyk & Chebotar, 2000, Plant Breeding 119: 363 364), and indeterminate gametophyte (ig) mutation (Kermicle 1969 Science 166:1422 1424). The disclosures of which are incorporated herein by reference. Wide hybridization crosses can also be used to produce haploids. This method is sometimes referred to as the bulbosum method (Kasha and Kao, 1970, Nature 225:874-876). This method of haploid production occurs due to the elimination of the chromosomes from the pollinating parent.

EXAMPLES

The following examples are for illustrative purposes and are not intended to limit the scope of the disclosure. Those of skill in the art, in light of the present disclosure, would appreciate that many changes can be made in the specific embodiments which are disclosed and still obtain a like or similar result without departing from the scope of the disclosure.

Example 1

Generation of Double Haploid Plants in the Greenhouse Using 1,2,3-Trimethoxy-4-((1S,6R)-6-nitro-cyclohex-3-enyl)-benzene (compound 1) via Seedling Soaking This example demonstrates the use of an aryl-substituted cycloalkene to obtain doubled haploid plants by a chromosome doubling approach. An exemplary cycloalkene, 1,2,3-Trimethoxy-4-((1S,6R)-6-nitro-cyclohex-3-enyl)-benzene, designated as compound 1 was used to determine double haploid efficiency, doubling rate by a coleoptile tip cutting, seedling soaking method. Other doubling agents such as colchicine, pronamide, oryzalin and chlorpropham were used for comparative purposes. Data provided in Tables 1, 2 and 3 were generated using haploid seeds obtained through cross pollination of a maize line of interest with an inducer maize line.

The resulting maize seeds were sorted based on marker gene color.

Coleoptile tips in maize seedlings were cut and the seedlings were soaked in various chromosome doubling agents as shown in Table 1. Haploid maize seeds were germinated and the coleoptile tips were excised (1-2 mm). The seedlings were then soaked in the specified concentrations indicated in Table 1. Seedlings that survived were transplanted and grown until tassels and silk formed. Plants that produced tassels and silk were self-pollinated. Seeds produced form the self-pollination were visually assessed for the marker to identify them as double haploid (dihaploid). For the cycloalkene designated as compound 1, the doubling rate was about 53% at 5 μM and 76.5% at 125 μM. The doubling rate of the tested cycloalkene is comparable to colchicines treatment at 0.06% w/v. Surprisingly, the mortality rate for compound 1 at 5 μM is only 15.1% (10/66*100) and even at a higher 25 μM concentration is only 30.3% as compared to a mortality rate of 41.5% for colchicine.

Example 2

Generation of Double Haploid Plants in the Field Using 1,2,3-Trimethoxy-4-((1S,6R)-6-nitro-cyclohex-3-enyl)-benzene (compound 1) via Seedling Soaking The procedure listed in example 1 was utilized to treat maize seedlings that were subsequently transplanted into the field. Seedlings that survived the transplanting were grown to maturity. Plants that produced tassels and silk were self-pollinated. Seeds produced from the self-pollination were visually assessed for the marker to identify them as double haploid (dihaploid). Table 2 contains the data gathered for the doubling rate and pollination success. For the 0.06% w/v colchicine treatment, about 49 haploid plants were pollinated and about 38 plants had doubled haploid ears, resulting in a success rate of about 77.5% (38/49*100). For the cycloalkene treatment, 25 μM and 100 μM concentrations of compound Compound 1 was used. The 25 μM concentration had a success rate of 90% (36 out of 40 pollinated maize haploid plants had doubled haploid ears). For the 100 μM treatment, 15 out of 24 pollinated haploid maize plants had doubled haploid ears, resulting in a success rate of 62.5%.

Example 3

Generation of Double Haploid Plants Using 1,2,3-Trimethoxy-4-((1S,6R)-6-nitro-cyclohex-3-enyl)-benzene (compound 1) via Foliar Application Haploid maize seeds were planted in Sun Gro METRO-MIX® 360 planting mixture, which typically has a pH of 6.0 to 6.8 and an organic matter content of about 30 percent, in 72-well, plastic propagation flats (Dillen Products; Middlefield Ohio). When required to ensure good germination and healthy plants, a fungicide treatment and/or other chemical or physical treatment was applied. The plants were grown in a greenhouse with an approximate 15 hour photoperiod which was maintained at about 23-29° C. during the day and 22-28° C. during the night until they reached the V1-V3 growth stage. Nutrients and water were added on a regular basis and supplemental lighting was provided with overhead metal halide 1000-Watt lamps as necessary.

A weighed amount of compound 1, determined by the rate to be tested, was dissolved in 1.2 mL of dimethyl sulfoxide (DMSO) to obtain concentrated stock solutions. If the test compound did not dissolve readily, the mixture was warmed and/or sonicated. The concentrated stock solutions obtained were diluted with 10.8 mL of an aqueous mixture containing 1.25% v/v (volume/volume) Agri-dex Crop Oil Concentrate. Compound requirements are based upon a 12 mL application volume at a rate of 187 L/ha. Formulated compounds were applied to the plant material with an overhead Mandel track sprayer equipped with a 8002E nozzle calibrated to deliver 187 L/ha over an application area of 0.503 square meter at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. Approximately 14 days after treatment, the treated plants were transplanted to individual pots containing Sun Gro METRO-MIX® 360. Plants that produced tassels and silk were then self-pollinated to obtain dihaploid seed.

Table 3 illustrates the results of doubling rate after spray treatment with the chemicals of interest. In comparison with the seedling soaking treatment method, spray treatment of maize at the V1-V3 stage did not result in significant plant stress, therefore, the corn plants grew normally with no increase in mortality. The spray treated plant tassels and silks were synchronized well and the plants shed more pollen. This resulted in a doubling rate from 31-46%.

In addition to the low mortality rates in plants, the cycloalkene designated as compound 1, exhibits low toxicity in mammalian systems. For example, cochicine shows oral $LD_{50}$ (rat) of 5.89 mg/kg, whereas compound 1 shows $LD_{50}$ (rat) that is greater than or equal to 500 mg/kg. Eye irritation for colchicine is often observed for rabbit at about 1%/3D and whereas for compound 1, in response to a dose of about 100 mg/animal, 1 of 3 animals showed corneal and iridal effects at 24 hours that was resolved within 48 hrs. No dermal toxicity was observed for compound 1 on rats at 200 mg/kg and no skin irritation was observed for 250 mg/animal over a 7 day period on rabbits.

Therefore, this example demonstrates that the exemplary cycloalkene, 1,2,3-Trimethoxy-4-((1S,6R)-6-nitro-cyclohex-3-enyl)-benzene, designated as compound 1, functions as an effective chromosome doubling agent and results in fewer deaths in plants when compared to conventional agents such as colchicines.

TABLE 1

Chemical treatment using coleoptile tip cutting and then seedling soaking method) for haploid germinated maize seedlings.

| Treatment | Rate (µM) | No. plants alive | No. plants dead | No. plants TP | No. plants dead after TP | No. false haploid plants | No. plants left | No. plants with pollen & silks | % DR |
|---|---|---|---|---|---|---|---|---|---|
| Pronamide | 125 | 2 | 62 | 1 | 0 | 1 | N/A | N/A | |
| Pronamide | 25 | 13 | 51 | 12 | 1 | 6 | 5 | 2 | |
| Pronamide | 5 | 41 | 23 | 40 | 3 | 10 | 27 | 12 | 44.5 |
| Oryzalin | 125 | 26 | 36 | 25 | 0 | 6 | 19 | 4 | 21 |
| Oryzalin | 25 | 40 | 24 | 29 | 1 | 6 | 22 | 7 | 31.8 |
| Oryzalin | 5 | 58 | 6 | 58 | 3 | 13 | 42 | 14 | 33.3 |
| Chlorpropham | 125 | 0 | 64 | 0 | 0 | N/A | N/A | N/A | |
| Chlorpropham | 25 | 1 | 63 | 1 | 0 | 1 | N/A | N/A | |
| Chlorpropham | 5 | 16 | 48 | 16 | 0 | 5 | 11 | 5 | 45.5 |
| Colchicine | | 38 | 27 | 37 | 0 | 7 | 30 | 16 | 53.3 |
| Compound 1 | 125 | 29 | 34 | 24 | 2 | 5 | 17 | 13 | 76.5 |
| Compound 1 | 25 | 46 | 20 | 44 | 2 | 10 | 32 | 20 | 62.5 |
| Compound 1 | 5 | 56 | 10 | 56 | 2 | 9 | 45 | 24 | 53.3 |

TP—transplanted; DR—doubling rate (No. plants with pollen and silk/No. of plants left * 100)

TABLE 2

Doubled haploid success rates for various chemical treatments in the field for maize.

| Treatment | % haploid maize plants pollinated (doubling rate) | % DH pollination success |
|---|---|---|
| 0.06% colchicine | 55.68 | 77.55 |
| Compound 1, 25 µM | 67.79 | 90 |
| Compound 1, 100 µM | 51.06 | 62.5 |

DH—doubled haploid

TABLE 3

Spray treatment of germinated haploid maize seedlings in soil at V1-V3 stage.

| Treatment | Rate (g ai/ha) | # of seedings sprayed | # plants dead after treatment | # plants rogued out (false haploid seeds) | # plants w/pollen and silk | % DR |
|---|---|---|---|---|---|---|
| Compound 1 | 70 | 24 | 0 | 5 | 6 | 31.2 |
| Compound 1 | 280 | 33 | 0 | 7 | 12 | 46.2 |

TABLE 3-continued

Spray treatment of germinated haploid maize seedlings in soil at V1-V3 stage.

| Treatment | Rate (g ai/ha) | # of seedings sprayed | # plants dead after treatment | # plants rogued out (false haploid seeds) | # plants w/pollen and silk | % DR |
|---|---|---|---|---|---|---|
| Pronamide | 35 | 19 | 0 | 1 | 5 | 27.8 |
| Pronamide | 140 | 22 | 0 | 4 | 3 | 16.7 |
| Chlorpropham | 70 | 24 | 0 | 2 | 9 | 40.9 |
| Chlorpropham | 280 | 34 | 1 | 2 | 18 | 58.1 |

DR—doubling rate

The invention claimed is:

1. A method for generating a doubled haploid corn plant cell, the method comprising:
    contacting a population of haploid corn plant cells with a composition comprising 1,2,3-trimethoxy-4-((1S,6R)-6-nitro-cyclohex-3-enyl)-benzene in a concentration between about 5 µM and about 125 µM; and
    generating a doubled haploid corn plant cell from the population at a rate of from about 40% to about 75%.

2. The method according to claim 1, wherein the composition comprises dimethyl sulfoxide.

3. The method according to claim 1, wherein the composition comprises an agriculturally acceptable surfactant.

4. The method according to claim 1, wherein the population of haploid corn plant cells is a seedling.

5. The method according to claim 1, wherein the population of haploid corn plant cells is a root.

6. The method according to claim 1, wherein the population of haploid corn plant cells is an embryo.

7. The method according to claim 1, wherein the population of haploid corn plant cells is a haploid cell culture.

8. The method according to claim 1, further comprising the step of generating a whole doubled haploid corn plant from the doubled haploid corn plant cell.

9. The method according to claim 1, further comprising the step of generating a doubled haploid corn seed from the doubled haploid corn plant cell.

10. The method according to claim 8, wherein the whole doubled haploid corn plant produces a seed comprising a doubled haploid embryo, and the doubled haploid embryo has a first and a second set of chromosomes that are homozygous.

11. The method according to claim 1, wherein the haploid corn plant cell is obtained from a haploid corn seed derived from a cross-pollination with an inducer line.

12. The method according to claim 1, wherein the method comprises obtaining the population of haploid corn plant cells by pollinating a corn ear with an inducer line.

13. The method according to claim 1, wherein contacting the haploid corn plant cell with the composition comprises:
    soaking a seedling comprising the haploid corn plant cell in the composition, or
    contacting a leaf tissue comprising the haploid corn plant cell with the composition.

14. The method according to claim 1, wherein contacting the haploid corn plant cell with the composition comprises injecting a base of a corn ear with the composition.

15. The method according to claim 12, wherein the inducer line is selected from the group consisting of stock 6, stock 6 derivatives, stocks carrying an indeterminate gametophyte (ig) mutation, RWS, KEMS, KMS, ZMS and MNL.

16. The method according to claim 1, wherein the method does not comprise selfing or crossing a plant comprising the plant cell to generate the doubled haploid plant cell.

17. The method according to claim 1, wherein the method consists essentially of contacting the haploid corn plant cell with the composition.

\* \* \* \* \*